United States Patent
Chojin

(10) Patent No.: US 8,388,646 B2
(45) Date of Patent: *Mar. 5, 2013

(54) MONOCOQUE JAW DESIGN

(75) Inventor: Edward M. Chojin, Boulder, CO (US)

(73) Assignee: Covidien LP, Mansfield, MA (US)

( * ) Notice: Subject to any disclaimer, the term of this patent is extended or adjusted under 35 U.S.C. 154(b) by 596 days.

This patent is subject to a terminal disclaimer.

(21) Appl. No.: 12/361,369

(22) Filed: Jan. 28, 2009

(65) Prior Publication Data

US 2009/0216229 A1 Aug. 27, 2009

Related U.S. Application Data

(60) Provisional application No. 61/030,771, filed on Feb. 22, 2008.

(51) Int. Cl.
*A61B 17/00* (2006.01)
*B23P 19/04* (2006.01)

(52) U.S. Cl. ........... 606/206; 606/207; 606/208; 29/238

(58) Field of Classification Search .......... 606/205–209, 606/51, 52; 29/887, 527.1, 527.2, 244, 238, 29/239, 270

See application file for complete search history.

(56) References Cited

U.S. PATENT DOCUMENTS

| | | | |
|---|---|---|---|
| 5,318,589 A | 6/1994 | Lichtman | |
| 5,665,100 A | 9/1997 | Yoon | |
| 5,759,188 A | 6/1998 | Yoon | |
| 5,797,927 A | 8/1998 | Yoon | |
| 5,954,731 A | 9/1999 | Yoon | |
| 6,099,550 A | 8/2000 | Yoon | |
| 6,334,860 B1 | 1/2002 | Dorn | |
| 6,685,724 B1 | 2/2004 | Haluck | |
| 2005/0159745 A1 | 7/2005 | Truckai et al. | |
| 2007/0106297 A1* | 5/2007 | Dumbauld et al. | 606/51 |
| 2009/0198233 A1* | 8/2009 | Chojin | 606/48 |

FOREIGN PATENT DOCUMENTS

EP 1 810 625 7/2007

OTHER PUBLICATIONS

European Search Report for corresponding European Appln. No. EP 09 15 3423 dated Jul. 10, 2009.

* cited by examiner

*Primary Examiner* — Nicholas Lucchesi
*Assistant Examiner* — Pritesh Patel

(57) ABSTRACT

A jaw member for use with an electrosurgical forceps includes a support member having a first surface and a pair of depending sides which extend therefrom forming a generally U-shaped configuration. The free end of the sides each including a flange which extends outwardly therefrom which is designed to attach to an electrically conductive plate such that the plate bridge the two flanges to enclose the U-shaped support member to form a box-like skeleton having a cavity defined therein. An insulative material is disposed within the cavity and an insulative cover is disposed about a periphery of the box-like support skeleton to insulate surrounding tissue during activation of the conductive plate.

10 Claims, 6 Drawing Sheets

MONOCOQUE JAW DESIGN

CROSS-REFERENCE TO RELATED APPLICATIONS

This application claims the benefit of priority to U.S. Provisional Application Ser. No. 61/030,771 entitled "MONOCOQUE JAW DESIGN" filed Feb. 22, 2008 by Edward Chojin, which is incorporated by reference herein.

BACKGROUND

1. Technical Field

The present disclosure relates to an electrosurgical forceps and, more particularly, the present disclosure relates to a method of manufacturing jaw members for an end effector assembly for use with either an endoscopic or open bipolar and/or monopolar electrosurgical forceps.

2. Background of Related Art

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

A general issue with existing electrosurgical forceps is that the jaw members are constructed to include a steel structural support member, which typically requires precise machining and assembly making the jaw member manufacturing process costly and time consuming.

SUMMARY

The present disclosure relates to a method for manufacturing a jaw member and includes the initial step of providing a conductive plate and a support member. The support member includes a flange extending therefrom (e.g., on the tip, around the perimeter, and/or along the length, etc.). The method also includes the steps of: attaching the conductive plate to the flange to form a box-like support skeleton having a cavity defined therein; inserting a filler material into the cavity to maintain a rigid support and to add strength to the jaw member as the conductive plate presses against the support member; and an outer insulative cover disposed on an outer periphery of the box-like support skeleton with an insulative cover. In embodiments the filler material may be insulative or conductive. The filler material and the insulative cover may be made from similar material and may include plastic, epoxy, polymer-based materials, resin, carbon fiber, gel and combinations thereof.

In one embodiment, the step of attaching the conductive plate to the support member to form a box-like support skeleton includes at least one of welding, soldering, gluing and mechanically engaging. In another embodiment, the support member may be stamped to form a substantially U-shaped configuration. In other embodiments, the support member may have any other suitable shape, for example, a substantially partial O-shaped configuration, or a substantially V-shaped configuration. In still another embodiment, the conductive plate includes a knife slot defined therein.

The present disclosure also relates to a method for manufacturing a jaw member and includes the steps of: providing a conductive plate and a U-shaped support member having flanges and which extend therefrom; attaching the conductive plate to the flanges along a length thereof to form a box-like support skeleton having a cavity defined therein; inserting an insulative material into the cavity to insulate and support the conductive plate against the U-shaped support member; and attaching an insulative cover to an outer periphery of the box-like support skeleton to insulate tissue from the support structure.

The present disclosure also relates to a jaw member for use with an electrosurgical forceps having a support member with a first surface and a pair of depending sides which extend therefrom forming a generally U-shaped configuration. The free end of each side includes a flange which extends outwardly therefrom. A conductive plate connects to an electrosurgical energy source and is welded to the support member to bridge the flanges and enclose the support member to form a box-like skeleton having a cavity defined therein. An insulative material is disposed within the cavity to provide structural support to the conductive plate and an insulative cover is disposed about a periphery of the box-like support skeleton to insulate surrounding tissue during activation of the conductive plate.

BRIEF DESCRIPTION OF THE DRAWINGS

Various embodiments of the subject instrument are described herein with reference to the drawings wherein.

DETAILED DESCRIPTION

Figure 1A:
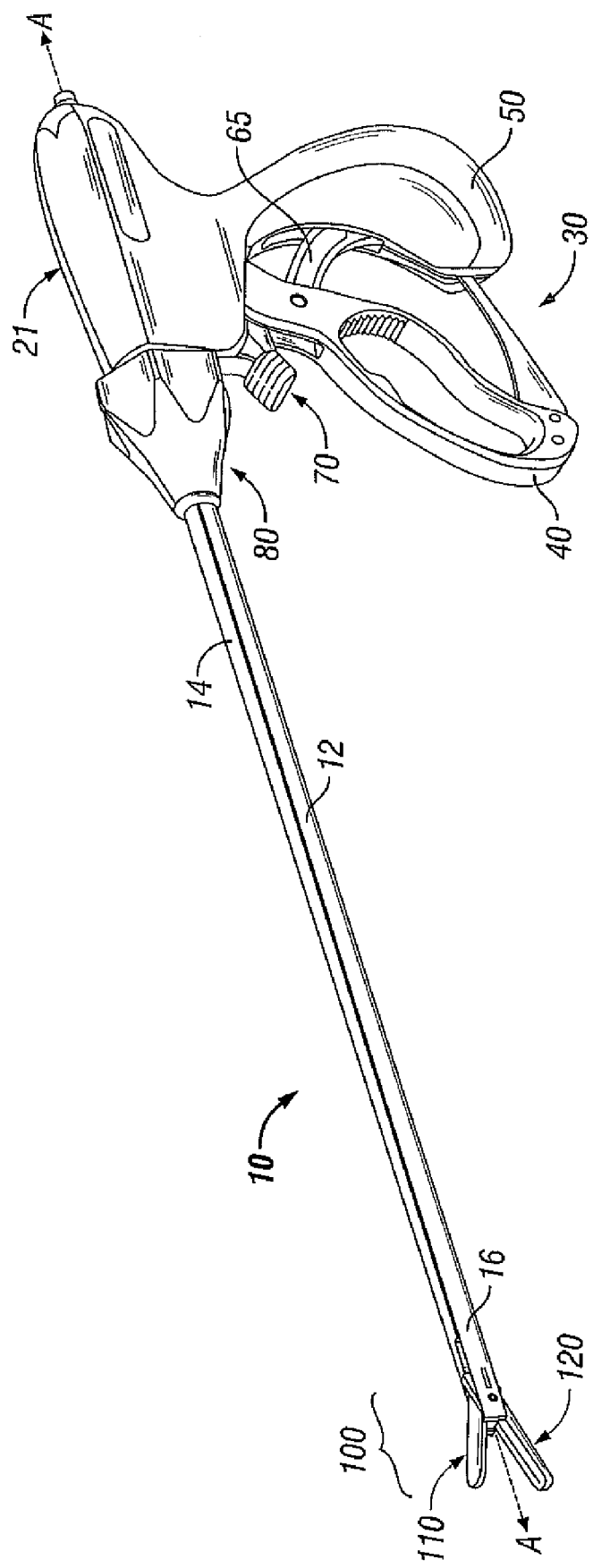
FIG. 1A is a perspective view of a pistol-grip style endoscopic bipolar forceps having a housing, a shaft and an end effector assembly according to one embodiment of the present disclosure.

Embodiments of the presently disclosed electrosurgical instrument are described in detail with reference to the drawing figures wherein like reference numerals identify similar or identical elements. As used herein, the term "distal" refers to that portion which is further from the user while the term "proximal" refers to that portion which is closer to the user or surgeon.

One embodiment of a forceps for use with the present disclosure includes a pistol-grip style endoscopic forceps 10 shown in FIG. 1A. Forceps 10 includes a housing 20, a handle assembly 30, a rotating assembly 80, a trigger assembly 70 and an end effector assembly 100 that mutually cooperate to grasp, seal and divide tubular vessels and vascular tissue. For the purposes herein, forceps 10 will be described generally, however, the various particular aspects of this particular forceps are detailed in commonly owned U.S. Pat. No. 7,083,618.

Forceps 10 also includes a shaft 12 that has a distal end 16 dimensioned to mechanically engage the end effector assembly 100 and a proximal end 14 that mechanically engages the housing 20 through rotating assembly 80. As will be discussed in more detail below, the end effector assembly 100 includes a monocoque jaw design. The term monocoque as used herein is defined as a structure in which the outer skin or shell carries all or most of the torsional and bending stresses, or a structure in which the body is integral with and shares the stresses with the chassis.

Forceps 10 also includes an electrosurgical cable 310 that connects the forceps 10 to a source of electrosurgical energy, e.g., a generator (not shown). The generator includes various safety and performance features including isolated output, independent activation of accessories, and Instant Response™ technology (a proprietary technology of Valleylab, Inc., a division of Tyco Healthcare Group, LP) that provides an advanced feedback system to sense changes in tissue many times per second and adjust voltage and current to maintain appropriate power. Cable 310 is internally divided into a series of cable leads (not shown) that each transmit electrosurgical energy through their respective feed paths through the forceps 10 to the end effector assembly 100.

Handle assembly 30 includes handles 40 and 50; handle 40 is movable relative to handle 50 from a first spaced apart position wherein the end effector assembly 100 is disposed in an open position to a second position wherein the end effector assembly 100 is positioned to engage tissue. Rotating assembly 80 is operatively associated with the housing 20 and is rotatable in either direction about a longitudinal axis "A". Details of the handle assembly 30 and rotating assembly 80 are described in the above-referenced patent, namely, U.S. Pat. No. 7,083,618.

Figure 1B:
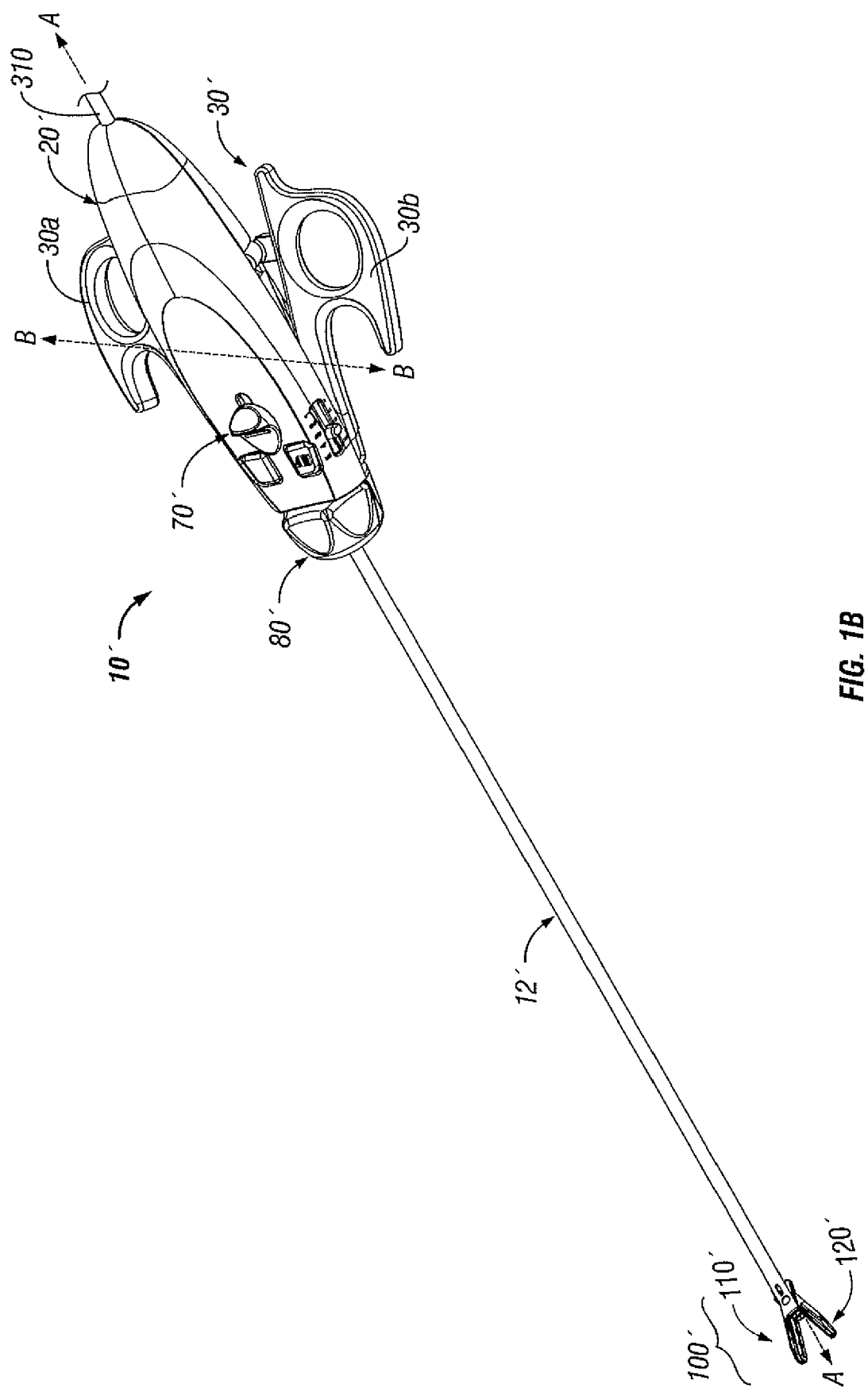
FIG. 1B is a perspective view of an in-line endoscopic bipolar forceps having a housing, a shaft and an end effector assembly according to another embodiment of the present disclosure.

FIG. 1B shows a so called "in-line" endoscopic forceps 10' for use with various surgical procedures and generally includes similar elements as described above (e.g., handle assembly 30', housing 20', rotating assembly 80', trigger assembly 70', shaft 12' and end effector assembly 100') that, together, mechanically cooperate to impart movement of the jaw members 110' and 120' from an open position wherein the jaw members 110' and 120' are disposed in spaced relation relative to one another, to a clamping or closed position wherein the jaw members 110' and 120' cooperate to grasp tissue (not shown) therebetween. Handle assembly 30' includes two opposing handles 30a and 30b that are each movable relative to housing 20' from a first spaced apart position wherein the end effector assembly 100' is disposed in an open position to a second position closer to housing 20' wherein the end effector assembly 100' is positioned to engage tissue. Rotating assembly 80' is operatively associated with the housing 20' and is rotatable in either direction about a longitudinal axis "A". The various particular aspects of this particular forceps are detailed in commonly owned U.S. patent application Ser. No. 11/540,335.

For the purposes herein, forceps 10 is discussed in further detail with respect to the monocoque jaw assembly of the present disclosure; however, it is envisioned that either endoscopic forceps 10 or 10' may include the presently disclosed jaw design.

Figure 2A:
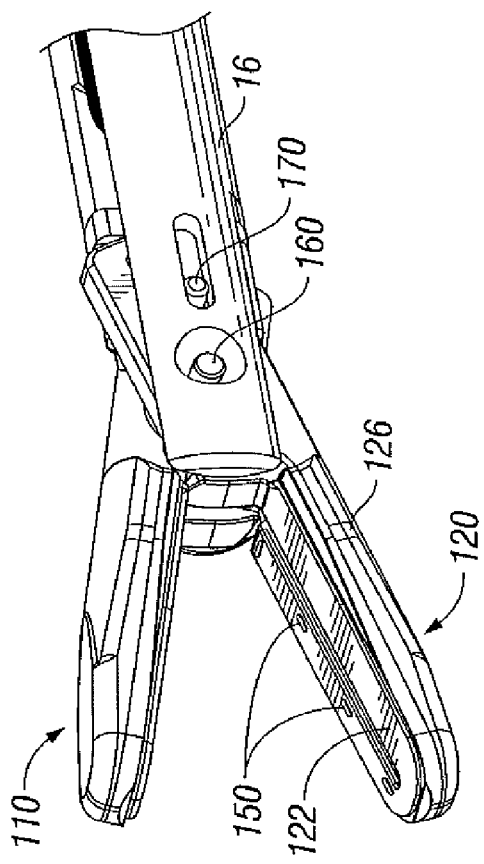
FIG. 2A is an enlarged, perspective view of the end effector assembly of FIG. 1A.
Figure 2B:
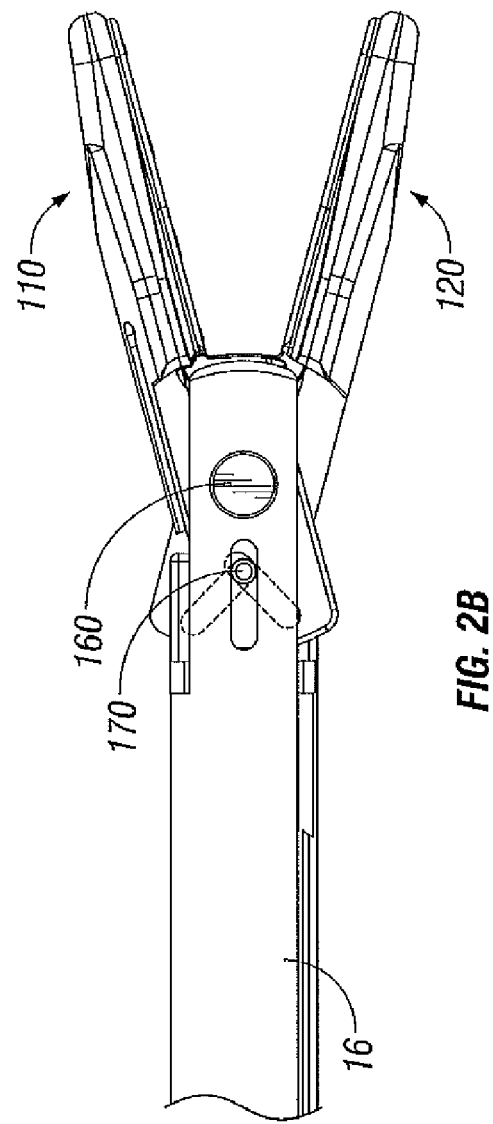
FIG. 2B is an enlarged, side view of the end effector assembly of FIG. 1A.

As mentioned above, and as shown best in FIGS. 2A and 2B, end effector assembly 100 is attached at the distal end 16 of shaft 12 and includes a pair of opposing jaw members 110 and 120. Movable handle 40 of handle assembly 30 is ultimately connected to a drive assembly (not shown) that, together, mechanically cooperate to impart movement to a drive pin 170 which, in turn, cams the jaw members 110 and 120 about pivot 160 from an open position wherein the jaw members 110 and 120 are disposed in spaced relation relative to one another, to a clamping or closed position wherein the jaw members 110 and 120 cooperate to grasp tissue therebetween. Other suitable methods of closing and/or opening jaw members are contemplated in the art such as reciprocating closure tube assemblies, gear mechanisms, camming mechanisms, rack and pinion systems, pulley systems, etc.

Figure 3:
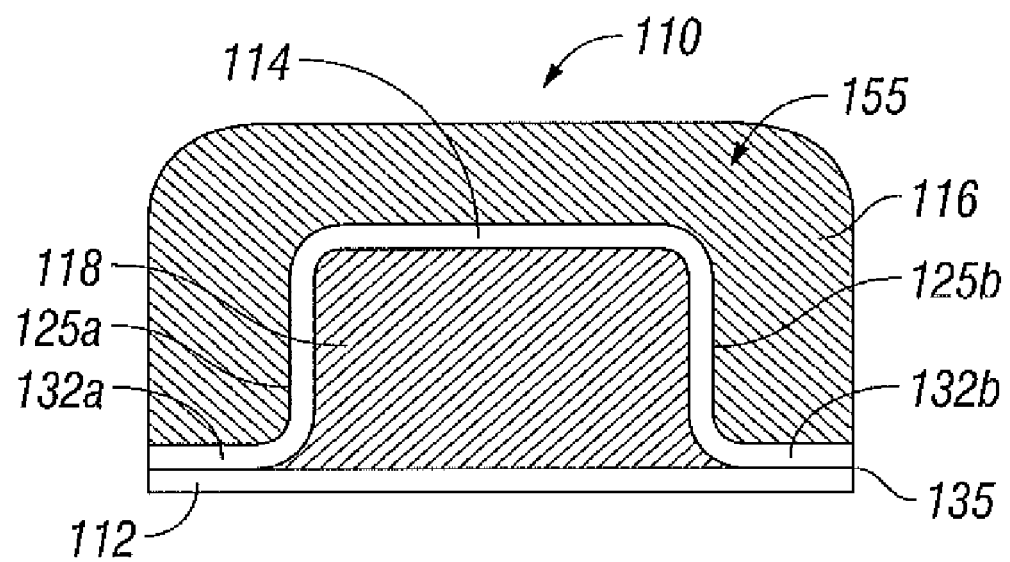
FIG. 3 is an enlarged, cross sectional view of a bipolar jaw member according to one embodiment of the present disclosure.
Figure 4:
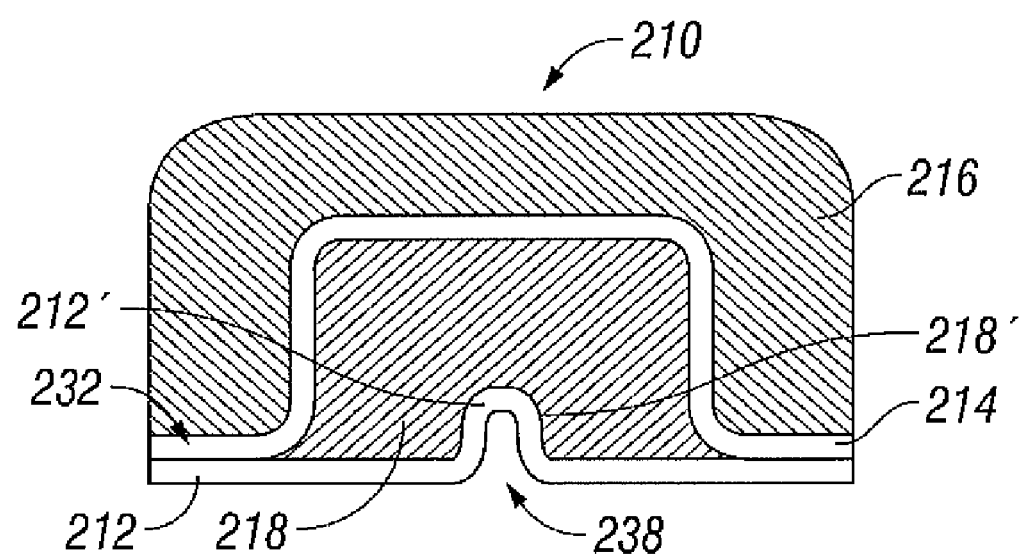
FIG. 4 is an enlarged, cross sectional view of a bipolar jaw member according to another embodiment of the present disclosure.
Figure 5:
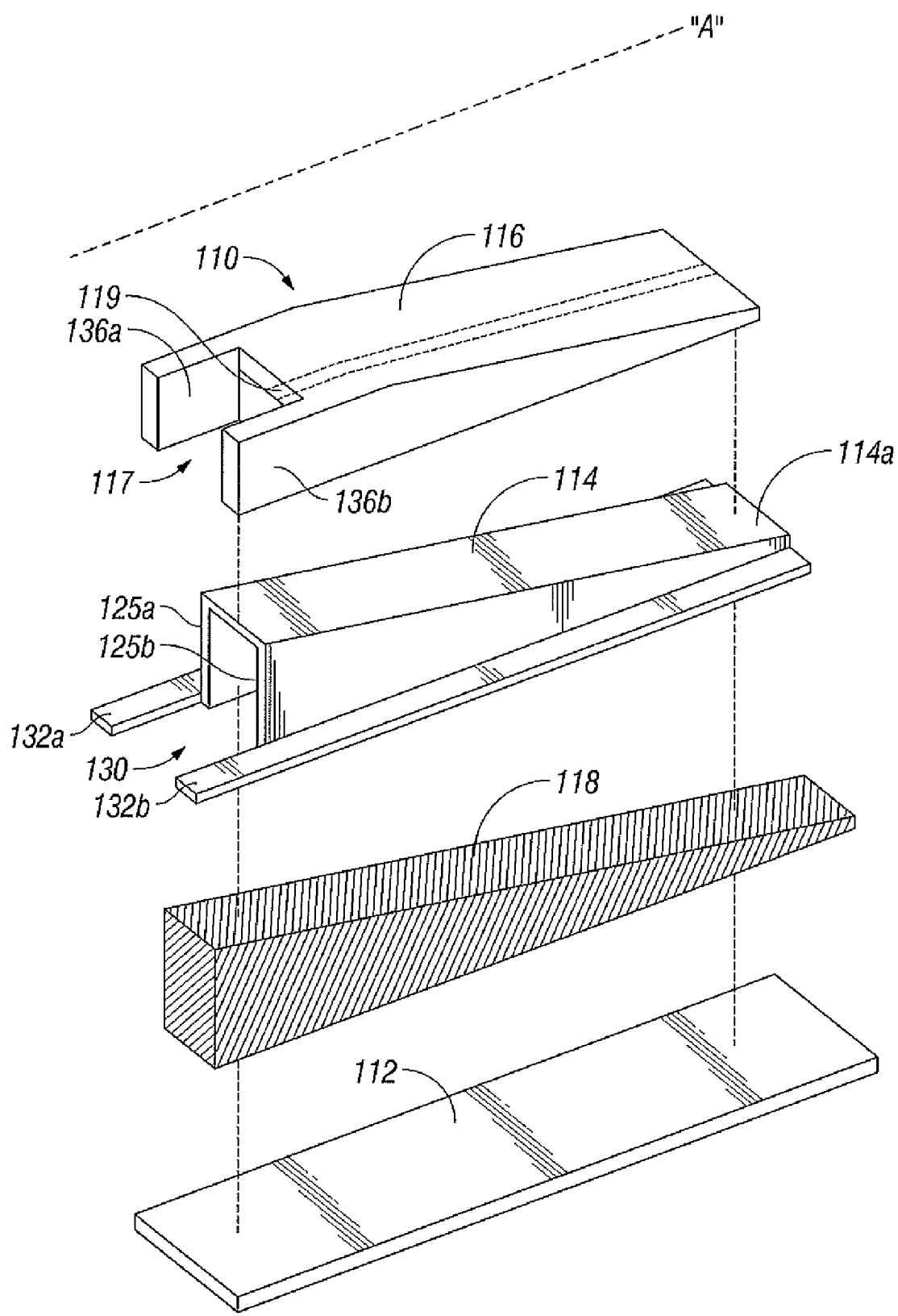
FIG. 5 is an enlarged, exploded view of the bipolar jaw member of FIG. 3.

Turning now to the figures, FIGS. 3-6, the present disclosure describes various embodiments of a monocoque jaw design and methods for manufacturing the same. More particularly, FIGS. 3 and 5 show one embodiment of a monocoque jaw member 110 that includes an electrically conductive or sealing plate 112, a support member 114, an insulative cover 116, and a filler material 118 that could be conductive or insulative, depending upon a particular or desired configuration. In this instance, jaw member 120 includes similar elements (e.g., conductive seal plate 122, insulative housing 126) as described above with respect to jaw member 110 and as further described below. After assembly of each monocoque jaw member, the two jaw members 110 and 120 are then assembled to move about a common pivot, e.g., pivot 160 as described above with respect to FIGS. 1A-2B.

Support member 114 may be constructed from any suitable metal contemplated in the art and may be stamped or otherwise formed to include a generally U-shaped configuration with an outer surface 114a and two downwardly depending sides 125a and 125b. The support member 114 may also be stamped in various other shaped configurations, for example, an substantially V-shaped configuration, a substantially O-shaped configuration, or any other suitable shaped configuration.

In another embodiment a pair of flanges 132a and 132b extend outwardly from the free ends of sides 125a and 125b, respectively, and are configured to run along the length of support member 114 creating a peripheral lip. The U-shaped support member 114 thereby defines an inner cavity 130 configured to receive the filler material 118 as described in more detail below.

Insulative cover 116 is configured to encapsulate support member 114 and may be formed from any suitable material, such as plastic, epoxy, resin, gel, polymer-based materials, so-called cool polymers, etc. Cover 116 may be mechanically engaged atop support member 114, may be formed in a die plate, or injection molded as part of a manufacturing step so long as insulative cover 116 protects surrounding tissue from electrical currents. More particularly, cover 116 (when formed) includes an inner surface 119 having two depending side surfaces 136a and 136b which together define a cavity 117 that is configured to encapsulate support member 114. Again, the inner surface 119 and sides 136a and 136b may be pre-formed in a die plate or injection molded to encapsulate the support member 114.

As mentioned above, jaw member 110 also includes a seal plate 112 and an filler material 118 disposed between the seal plate 112 and the support member 114. More particularly, the filler material 118 is configured to fit inside the cavity 130, which may be pre-formed in a die plate or injection molded into the support member 114. Filler material 118 may be formed from the same insulative material as the cover 116. Alternatively, as mentioned above, the filler material 118 may be conductive and may be formed from any suitable conductive material. For example, filler material 118 may be electrically insulative, thermally insulative, semi-conductive, or conductive according to a particular surgical purpose or to achieve a particular surgical result.

Upon assembly, the filler material 118 provides structural support for the support member 114 during load conditions, and under certain conditions may be adapted to thermally dissipate heat to facilitate consistent tissue treatment. As mentioned above, insulative cover 116 acts to insulate surrounding tissue, and under certain circumstances may be adapted to dissipate heat or thermal spread to surrounding tissue. Support member 114 is designed to off-load or carry part of the load during high pressure applications, such as vessel sealing, and also offload the torsional and bending stresses associated therewith.

Support member 114 may be configured to engage sealing plate 112 by welding, gluing, or other suitable engaging methods. For example, a weld 135 may run along the edge of sealing plate flanges 132a and 132b to securely engage sealing plate 112 to support member 114, thus forming the U-shaped monocoque jaw skeleton 155 (See FIG. 3). Filler material 118 is configured to be placed between inner cavity 130 of support member 114, thus increasing structural strength of the jaw member 110 and, in particular, providing rigidity to the sealing plate 112. Cover 116 is then overmolded or limited to encapsulate the support member 114 (and sealing plate 112/filler material 118 assembly) to electrically insulate surrounding tissue from the outer periphery of the jaw member 110.

FIG. 4 shows another similar embodiment of a jaw member 210 that includes a sealing plate 212 having a knife slot 238 defined along a length thereof. Jaw member 210 includes similar elements and is manufactured and assembled in a similar fashion as described above with respect to jaw member 110. For example, jaw member 210 includes a sealing plate 212, a filler material 218, a support member 214 and an insulative cover 216, that are assembled to form monocoque jaw member 210 with a knife channel 238 disposed thereal-ong configured to reciprocate a knife (not shown) for cutting tissue. Filler material 218 may also include a recess 218' therein that is configured to accommodate a resulting bulge 212' formed in the sealing plate 212 upon creation of the knife channel 238.

One of the sealing plates, e.g., seal plate 122 (See FIG. 2A) may include one or more stop members 150 disposed on or operatively associated with the inner facing surface of the electrically conductive sealing surface 122 to facilitate gripping and manipulation of tissue and to define a gap "G" (not explicitly shown) between opposing jaw members 110 and 120 during sealing and cutting of tissue. A series of stop members 150 may be employed on one or both jaw members 110 and 120 depending upon a particular purpose or to achieve a desired result. A detailed discussion of these and other envisioned stop members 150, as well as various manufacturing and assembling processes for attaching and/or affixing the stop members to the electrically conductive sealing surfaces 112, 122 are described in commonly-assigned U.S. Pat. No. 7,083,618.

Figure 6:
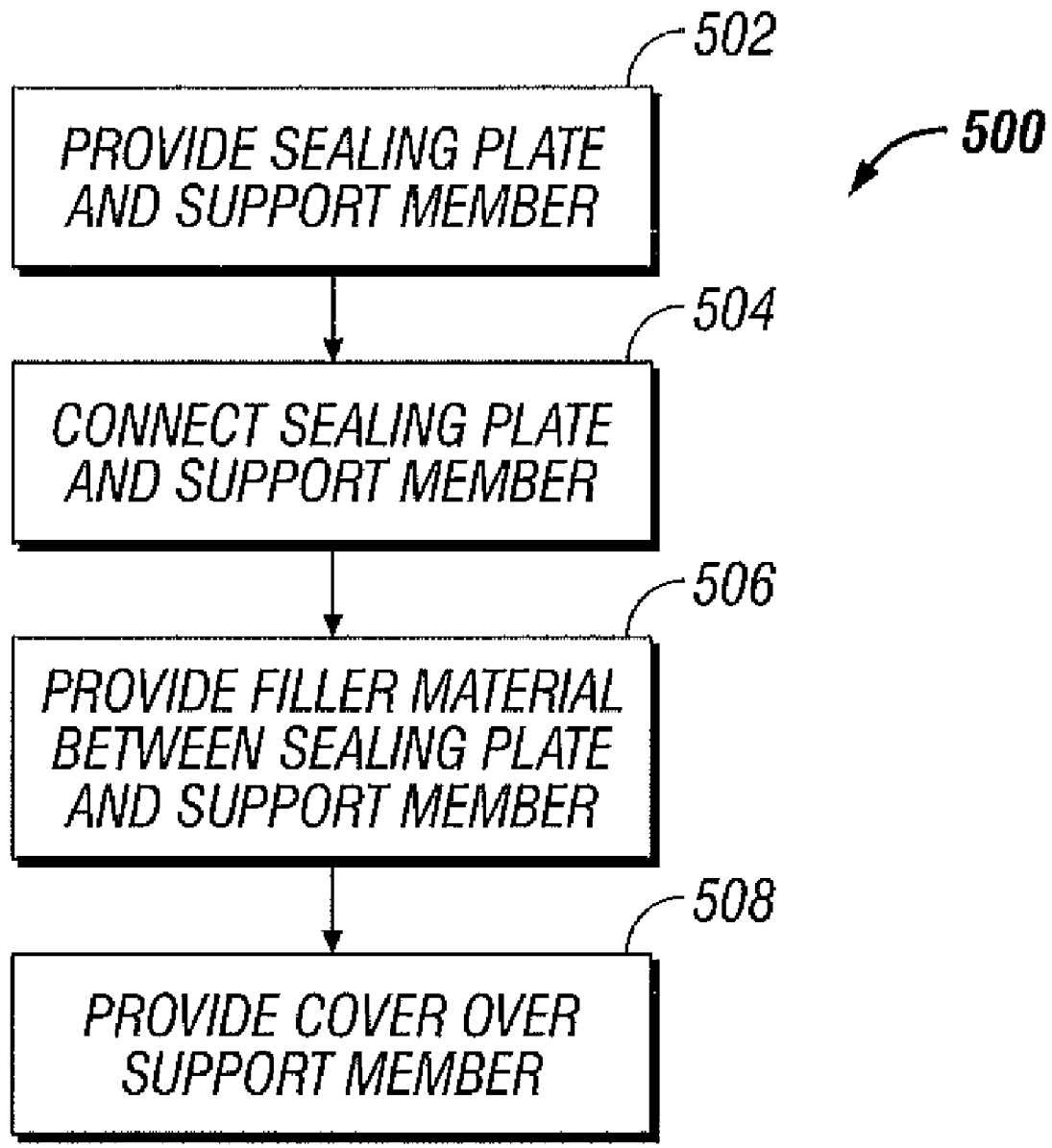
FIG. 6 is a flow chart showing a method of manufacturing a jaw member according to the present disclosure.

FIG. 6 shows a flowchart that illustrates a method 500 for manufacturing a monocoque jaw member according to the present disclosure. Method 500 includes step 502 of providing a seal plate 112 and a U-shaped support member 114 having flanges 132a and 132b which extend therefrom. Method 500 further includes step 504 of attaching the sealing plate 112 to the flanges 132a and 132b along a length thereof to form a box-like support skeleton 155 having a cavity 130 defined therein. At step 506, a filler material 118 is injected into the cavity 130 to bolster the support member 114. As mentioned above, filler material 118 may also insulate the inner cavity of the support member 114. Step 508 further includes overmolding an outer periphery of the box-like support skeleton 155 with an insulative cover 116.

The seal plate 212 of step 508 may be configured to include a knife channel 238 defined therein and may include one or more stop members 150 disposed therealong depending upon a particular surgical purpose. Step 504, which includes attaching the sealing plate to the flanges along a length thereof to form a box-like support skeleton, may include welding, soldering, gluing and mechanically engaging (e.g., pinching, crimping, riveting, shrink forming, etc.).

From the foregoing and with reference to the various figure drawings, those skilled in the art will appreciate that certain modifications can also be made to the present disclosure without departing from the scope of the same. For example, the cover 116 may be placed on support member 114 by overmolding (covering) a material on an outer surface of the support member 114 as mentioned above or by placing a pre-fabricated cover over support member 114. In addition, filler material 118 may also be pre-formed or pre-molded and inserted into cavity 130 to form the structural support for sealing plate 112.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A method for manufacturing a jaw member comprising the steps of:
 providing a conductive plate and a support member;
 attaching the conductive plate to the support member to form a box-like support skeleton having a cavity defined therein;
 inserting a filler material into the cavity to support the conductive plate against the support member; and
 forming an insulative cover on an outer periphery of the box-like support skeleton.

2. A method according to claim 1, wherein the step of attaching the conductive plate to the support member to form a box-like support skeleton includes at least one of welding, soldering, gluing and mechanically engaging.

3. A method according to claim 1, wherein the support member comprises at least one flange configured to extend therefrom.

4. A method according to claim 1, wherein the insulative cover is an overmold.

5. A method according to claim 1, wherein the insulative cover is a coating.

6. A method according to claim 1, wherein the support member is stamped to form at least one of a substantially U-shaped configuration, a substantially O-shaped configuration, and a substantially V-shaped configuration.

7. A method according to claim 1, wherein the filler material includes at least one of a plastic, epoxy, polymer-based material, resin, carbon fiber, gel and combinations thereof.

8. A method according to claim 1, wherein the insulative cover material includes at least one of a plastic, epoxy, resin, polymer-based material, gel, and combinations thereof.

9. A method according to claim 1, wherein the conductive plate includes a knife slot defined therein.

10. A method for manufacturing a jaw member comprising the steps of:
 providing a conductive plate and a U-shaped support member having flanges that extend therefrom;
 attaching the conductive plate to the flanges along a length thereof to form a box-like support skeleton having a cavity defined therein;
 injecting an insulative filler material into the cavity to insulate and support the conductive plate against the U-shaped support member; and
 attaching an insulative cover to an outer periphery of the box-like support skeleton.

* * * * *